United States Patent [19]

Molinari

[11] Patent Number: 5,547,946
[45] Date of Patent: Aug. 20, 1996

[54] TOPICAL PHARMACEUTICAL COMPOSITIONS FOR RESPIRATORY ALLERGIES

[75] Inventor: Giuliano Molinari, Bresica, Italy

[73] Assignee: Farmin S.r.l., Brescia, Italy

[21] Appl. No.: 152,476

[22] Filed: Nov. 15, 1993

[30] Foreign Application Priority Data

Nov. 18, 1992 [IT] Italy ................... BS92A0130

[51] Int. Cl.$^6$ .................. A61K 9/08; A61K 31/185; A61K 31/19
[52] U.S. Cl. .................. 514/129; 514/553; 514/557; 514/574; 514/578; 514/823; 514/826; 514/885
[58] Field of Search ................... 514/129, 553, 514/557, 574, 578, 823, 826; 574/885

[56] References Cited

U.S. PATENT DOCUMENTS

| | | | |
|---|---|---|---|
| 4,053,628 | 10/1977 | Stevenson et al. | 424/283 |
| 4,097,596 | 6/1978 | Begany et al. | 424/247 |
| 4,603,131 | 7/1986 | Bernstein et al. | 514/220 |
| 4,780,476 | 10/1988 | Grimminger et al. | 514/409 |
| 4,822,823 | 4/1989 | Yamamoto et al. | 514/690 |
| 4,900,730 | 2/1990 | Miyauchi | 514/12 |
| 4,950,776 | 8/1990 | Scolastico et al. | 558/169 |
| 4,983,595 | 1/1991 | Benjamin et al. | 514/174 |
| 5,124,315 | 6/1992 | Ceschel et al. | 514/12 |
| 5,126,432 | 6/1992 | Janis et al. | 530/350 |
| 5,128,332 | 7/1992 | Siren et al. | 514/103 |
| 5,202,130 | 4/1993 | Grant et al. | 424/167 |
| 5,281,586 | 1/1994 | Scolastico et al. | 514/129 |
| 5,284,839 | 2/1994 | Siren et al. | 514/103 |
| 5,306,840 | 4/1994 | Tronconi | 558/146 |
| 5,315,023 | 5/1994 | De Ferra et al. | 558/146 |
| 5,366,739 | 11/1994 | MacKeen | 424/602 |

FOREIGN PATENT DOCUMENTS

| | | |
|---|---|---|
| 0111841A1 | 12/1983 | European Pat. Off. . |
| 0241281A2 | 10/1987 | European Pat. Off. . |
| 0420598A2 | 9/1990 | European Pat. Off. . |
| 3409403A1 | 9/1985 | Germany . |
| 1561423 | 7/1977 | United Kingdom . |
| 2224932 | 10/1989 | United Kingdom . |
| 2245169 | 6/1991 | United Kingdom . |

*Primary Examiner*—Shep K. Rose
*Attorney, Agent, or Firm*—McGlew and Tuttle, P.C.

[57] ABSTRACT

A method and topical pharmaceutical composition for treating respiratory allergies, allergic rhinitis, allergic conjunctivitis, allergic asthma, and allergy to fur and dust, in which free ion calcium plays a role in a subject. The composition is in the form of oral local and/or nasal liquid solution or suspension for instillation, inhalation or insufflation and includes as active agent, at least one compound selected from the group consisting of: DL-α-glycerophosphoric acid, glutaric acid and their sodium or potassium salts as the essential active agent. The active agent, when supplied in a sufficient amount, being effective to enable by a reduction in free ion calcium concentration the removal or improvement in symptoms of allergy amenable to said free calcium ion concentration reduction.

14 Claims, No Drawings

TOPICAL PHARMACEUTICAL COMPOSITIONS FOR RESPIRATORY ALLERGIES

This invention relates to pharmaceutical compositions for local use which contain calcium complexing substances and are useful in the treatment of respiratory allergies.

It is estimated that 10% of the population in industrialized countries suffers from respiratory allergies, and that this figure is increasing. Under the heading of respiratory allergies are included well-known afflictions like allergic rhinitis, allergic conjunctivitis, allergic asthma and the various forms of allergy to fur, dust, etc.

There are numerous medicaments available for treatment of such afflictions, both for general as well as local use. More favored currently are local treatments in order to achieve the maximum therapeutic effect while minimizing the possibility of side effects.

These local treatments are generally administered by spray or aerosols: α-adrenergic decongestionants, (pseudoephedrine, phenylpropanolamine, oximethazoline, tramazoline), adrenergic bronchodilatators (epinephrine, isoproterenol, and the $\beta_2$ selective procaterol, salbutamol, terbutaline, pirbuterol and metaproterenol), antihistaminics (azelastine, levocabastine), corticosteroids (beclomethasone dipropionate, flunisolide) and the more specific sodium chromoglycate and ipatropium bromide (E. R. McFadden Jr. in "Harrison Principi di medicina interna" 1988, XI ed., 1355–61, McGraw Hill Italia; R. M. Naclerio, N. Engl. J. Med., 1991 Sep. 19, 325, 860–9).

The fundamental role played by calcium in many patho-physiological processes is well known, as it is also known in the allergic reactions. Although the mechanisms are different in each case and not always clearly understood, it is known that a variation of free calcium ion availability can affect the pathophysiological response. So, for example, a reduction in calcium concentration using antagonist substances will determine the reduction in the allergic asthma reaction (E. Middleton Jr., J. Pharm. Sci., 1980, 60/2, 243–50). These antagonists cause indirect reduction of calcium concentration, mainly acting as calcium channel blockers, or as calcium release blockers (P.M. Vanhoutte, Amer. J. Cardiol., 1987, 59:3A–8A).

Starting from these premises, it is the purpose of this invention to provide complexant-based pharmaceutical compositions for local use in the treatment of respiratory allergies. This use of calcium complexing substances has never been described in the previous literature; neither are the calcium antagonist substances listed in the above mentioned documents, nor the drugs so far proposed for allergy, able to form complexes with calcium at physiological conditions.

Unfortunately, many of the drugs so far mentioned have the disadvantage of producing unwanted side-effects even if administered locally. This fact has created worries amongst professional personnel for those patients who use excessive quantities of medicaments in the desire to remove irritating, though not serious, symptoms as quickly as possible (E. D. Meltzer, J. Occup. Med., 1990 Apr., 32/4, 327–34;E. Vaugham, Occup. Health Saf., 1991 Apr., 60/4, 28–30; F. Asole, Corriere della Sera, Medicina Pratica, 12 ott. 1992, 5).

The side-effects are particularly important during high dosage treatments of acute complaints or during pregnancy, lactation, in the treatment of infants (H. F. Krause in: Otolaryngologic clinics of North America, 1992, 25/1, 135–149) and in the reduction of bronchospasm, given that the therapeutic approach in the case of asthma is commonly based on the administration of more than one medicine (E. R. McFadden Jr. in: "Harrison Principi di medicina interna" 1988, XI ed. 1359, McGraw Hill Italia).

Therefore we have felt that research should be directed towards low-toxicity substances.

Now we have found, and that is precisely the subject of this invention, that some compounds capable of producing a reduction in the local availability of calcium ions, i.e. compounds that form either soluble or insoluble calcium complexes, enable the removal of or improvement in the condition of respiratory allergies such as allergic rhinitis, allergic bronchial asthma and other naso-bronchial obstructive air-passage conditions, other immediate hypersensitivity conditions, such as allergic conjunctivitis.

A preferred embodiment of the invention involves the utilization, as calcium-complexing substances, of pharmacologically acceptable organic and inorganic acids, their analogous substitutes, their functional derivatives and their salts. Particularly preferred are compounds having a high partition coefficient octanol/water, or/and a low molecular weight, never higher than 350 Dalton. Such compounds offer the advantage of a high transdermic absorption. Even more preferred are compounds, chosen from the normal constituents of the human organism, having a clearly-proven negligible toxicity. These offer the advantage of greater acceptability.

Examples of compounds utilized are the acids: carbonic acid, phosphoric acid, pyrophosphoric acid, DL-α-glycerophosphoric acid, phosphogluconic acid, phosphopyruvic acid, sulfuric acid, malonic acid, succinic acid, glutaric acid, fumaric acid, their analogous substitutes, their functional derivates and their pharmacologically acceptable salts. Examples of analogous substitutes are acids containing one or more additional groups of the types: alkyl-, aryl-, acyl-, oxo-, alkoxy-, hydroxy-, amino- etc. like malic acid, aspartic acid, N-acetylaspartic acid, acetylglycerophosphoric acid, phosphoxydroxypyruvic acid, citric acid, 2-oxosuccinic acid, α-keto-glutaric acid, glutamic acid, etc.

Examples of functional derivates are anhydrides, lactones, lactides, such as: carbonic anhydride, phosphogluconolactone, malic acid lactide, etc. Examples of pharmacologically acceptable salts are salts of lithium, sodium, potassium, iron and other non-toxic metals, ammonium, organic amines such as methylamine, diethylamine, monoethanolamine, piperazine, glucosamine, galactosamine, imidazole, etc.

TESTS OF PHARMACOLOGICAL ACTIVITY.

Three groups of volunteers were chosen, each of two men and two women, chosen on the basis of their medical complaint and the sensibility of their respiratory allergy. The first group demonstrated symptoms of allergic rhinitis; the second, rhinoconjunctivitis; the third, rhinopharyngitis associated with asthma.

After 8 weeks without treatment of antihistamines and 2 weeks without treatment of any other medicament, they were exposed to contact with allergenes and underwent tests for a week for each type of spray listed in the examples below. Between each spray test all treatments were suspended for a week, nor was any other medicine administered.

The treatment consisted of two oral spray applications of about 0.1 ml for the volunteers with symptoms of pharyngitis and asthma, and in two spray applications for each nostril for those with symptoms of rhinitis or rhinoconjunctivitis. In the case of severe rhinorrea the best results were obtained by increasing the number of spray applications so that the drug could penetrate the mucous wall and come into direct contact with the nasal epithelium.

The symptomatology of the three groups was noted in relation to the different treatments during the different weeks and it was seen that:

there were no significant differences in results between males and females;

the preparations of examples 1 and 3 had the best effects with a total remission of symptoms in 42% of the cases and attenuation in 50/58%;

the preparation of example 2 gave total remission of the symptoms in 8% of the cases and attenuation in 66%;

in all the cases of rhinopharyngitis treated with the preparations of examples 1 and 3 there was at least attenuation even in the asthmatic symptomatology;

in all the cases of rhinoconjunctivitis treated, ocular pruritus disappeared, on average within 6 minutes of the application;

effects relative to the other symptoms (rhinorrea, sneezing rate, pharyngal pruritus, bronchospasm) were noted on average 20 minutes after the application, while the therapeutic benefits were felt on average for the following 120 minutes.

In cases where longer protection is required, the active duration of the treatments can be extended using prodrugs, as the previously cited functional derivatives, or formulations that partially delay the pharmacological activity.

The compositions described here are useful in the local treatment of respiratory allergies and are recommended for use in preventive and curative therapy of, for example: allergic rhinitis, allergic bronchial asthma, and other nasobronchial obstructive air-passage conditions, other immediate hypersensitivity conditions such as allergic conjunctivitis. The compounds discussed in this document and used in the treatment of respiratory allergies are formulated in topical pharmaceutical compositions. The compositions, which contain one or more of the chemical compounds listed above and which are mixed with pharmaceutically acceptable excipients, fall within the limits of the invention. Topical pharmaceutical compositions can be prepared using conventional methods, such as those described in Remington's Pharmaceutical Sciences Handbook, Mac Pub. Co. XVII ed., N.Y., U.S.A.. Examples of pharmaceutical compositions in accordance with the invention are: solutions or suspensions for instillation, inhalation or insufflation. The pH of such compositions is neutral, or weakly basic. The vehicle for the composition is mainly an aqueous or organic solvent, or it may also be a mixture of the two. Other than solvents, there can be pharmaceutically acceptable excipients such as: dispersing agents, solubilizers, flavoring agents, antimicrobials, etc., as well as oils, or conventional carriers for the composition of delayed-release particles.

In all cases the proportion of active ingredients to the whole composition will be high enough for the desired activity with each application.

The prescribed doses differ according to the active ingredient, the formulation chosen, the type of preventive or curative treatment selected, and the severity of the symptoms to be treated.

The expected side effects from therapeutic doses are irrelevant. The following examples further illustrate the invention.

EXAMPLE 1

| Active agent: Sodium tribasic citrate Excipients: | 1.3 g |
| --- | --- |
| Menthol | 0.005 g |
| Antimicrobials | 0.01–0.20 g |
| Water | q.b. at 100 ml |

EXAMPLE 2

| Active agent: Sodium bibasic DL-α-glycerophosphate Excipients: | 1.1 g |
| --- | --- |
| Antimicrobials | 0.01–0.20 g |
| Water | q.b. at 100 ml |

EXAMPLE 3

| Active agent: Potassium bicarbonate Excipients: | 0.8 g |
| --- | --- |
| Antimicrobials | 0.01–0.20 g |
| Sorbitol | 3 g |
| Water | q.b. at 100 ml |

What is claimed is:

1. Topical pharmaceutical composition in the form of oral local and/or nasal liquid solution or suspension for instillation, inhalation or insufflation containing, as active agent, at least one compound selected from the group consisting of: DL-α-glycerophosphoric acid, glutaric acid and their sodium or potassium salts as the essential active agent for use in the treatment of respiratory allergies, allergic rhinitis, allergic conjunctivitis, allergic asthma or allergy to fur or dust and in which free ion calcium plays a role, said active agent, when supplied in a sufficient amount, being effective to enable by a reduction in free ion calcium concentration the removal or improvement in symptoms of allergy amenable to said free calcium ion concentration reduction.

2. Composition of claim 1 wherein the concentration of the active agent is between about 0.8% w/v and 1.3% w/v.

3. Composition of claim 1 wherein the active agent is sodium bibasic DL-α-glycerophosphate.

4. Composition of claim 1 wherein the active agent is sodium bibasic glutarate.

5. Composition of claim 1 wherein the solution or suspension is in nasal instillation topical dosage form.

6. Composition of claim 1 wherein the solution or suspension is in oral local and nasal inhalation topical dosage form.

7. Composition of claim 1 wherein the solution or suspension is in nasal and oral local insufflation topical dosage form.

8. Method of treating respiratory allergies, allergic rhinitis, allergic conjunctivitis, allergic asthma, and allergy to fur and dust and in which free ion calcium plays a role in a subject, comprising topically administrating to the subject a topical pharmaceutical composition, in accordance with claim 1, in the form of an oral local and/or nasal solution or suspension for instillation, inhalation or insufflation containing as essential active agent at least one compound selected from the group consisting of: DL-α-glycerophosphoric acid, glutaric acid and their sodium or potassium salts, having a molecular weight below about 350 Dalton and capable of forming a complex with calcium, said active agent, when supplied in a sufficient amount, being effective to enable, by reduction in free ion concentration, the removal or improvement in symptoms of allergy amenable to said free calcium ion concentration reduction.

9. Method of claim 8 wherein the concentration of the active agent is between about 0.8% w/v and 1.3% w/v.

10. Method of claim 8 wherein the active agent is sodium bibasic DL-$\alpha$-glycerophosphate.

11. Method of claim 8 wherein the active agent is sodium bibasic glutarate.

12. Method of claim 8 wherein the administration is effected by instillation.

13. Method of claim 8 wherein the administration is effected by inhalation.

14. Method of claim 8 wherein the administration is effected by insufflation.

* * * * *